(12) United States Patent
Onodera et al.

(10) Patent No.: US 7,820,371 B2
(45) Date of Patent: Oct. 26, 2010

(54) METHOD FOR REMOVING VIRUSES AND LEUKOCYTES FROM BLOOD USING A SURFACE COMPRISING HYDROXYL AND POLYETHYLENE GLYCOL GROUPS

(75) Inventors: Hirokazu Onodera, Oita (JP); Makoto Yoshida, Oita (JP)

(73) Assignee: Asahi Kasei Kuraray Medical Co., Ltd., Tokyo (JP)

( * ) Notice: Subject to any disclaimer, the term of this patent is extended or adjusted under 35 U.S.C. 154(b) by 654 days.

(21) Appl. No.: 11/772,448

(22) Filed: Jul. 2, 2007

(65) Prior Publication Data
US 2007/0248942 A1 Oct. 25, 2007

Related U.S. Application Data

(62) Division of application No. 10/492,652, filed as application No. PCT/JP02/10766 on Oct. 16, 2002, now abandoned.

(30) Foreign Application Priority Data
Oct. 16, 2001 (JP) ............... 2001-318512

(51) Int. Cl.
*A01N 1/02* (2006.01)
*B01D 11/00* (2006.01)
(52) U.S. Cl. .......................... 435/2; 210/645
(58) Field of Classification Search ............ None
See application file for complete search history.

(56) References Cited

U.S. PATENT DOCUMENTS

| 4,936,998 | A | 6/1990 | Nishimura et al. |
| 5,229,012 | A | 7/1993 | Pall et al. |
| 5,407,581 | A | 4/1995 | Onodera et al. |
| 6,600,014 | B2 | 7/2003 | Ogino et al. |
| 2004/0253204 | A1 | 12/2004 | Yagi et al. |
| 2006/0207937 | A1 | 9/2006 | Bonaguidi et al. |

FOREIGN PATENT DOCUMENTS

| EP | 0 972 530 | 1/2000 |
| JP | 2000 185094 | 7/2000 |
| JP | 2001-161807 | 6/2001 |
| JP | 2004-198215 | 7/2001 |
| JP | 2001-218834 | 8/2001 |
| WO | 01/66171 | 9/2001 |

OTHER PUBLICATIONS

English translation of JP 2000-229123, pp. 1-14, date of publication of original Japanese application, Aug. 22, 2000.*
English translation of JP 2000-245833, pp. 1-15, date of publication of original Japanese application , Sep. 9, 2000.*
Pileri et al., "Binding of Hepatitis C Virus to CD81", Science 282 : 938-941 (1998).*
Grant and Hackh's Chemical Dictionary, Definition of Terminal, p. 579, 1987.
Lipson et al., Cytomegalovirus Infectivity in Whole Blood Following Leukocyte Reduction by Filtration, AM J Clin, Pathol. 116: 52-55 (2001).
Barth et al, Efficacy of 2 Differenc Leukocyte Filters for Erythrocyte Concetrates, Schweizerische Medizinische Wochenschrift 123 (22): 1160=4 (1993).

* cited by examiner

*Primary Examiner*—Sandra Saucier
(74) *Attorney, Agent, or Firm*—Young & Thompson

(57) ABSTRACT

It is intended to provide a method whereby a virus and leukocytes can be simultaneously eliminated from virus-containing blood and platelets can be recovered at a high yield, and a material and an apparatus therefor. A water-soluble carrier having surface which is capable of capturing a virus and leukocytes in blood but allows the permeation of platelets therethrough is brought into contact with virus-containing blood. Thus the virus and leukocytes can be simultaneously removed from the blood while platelets can be recovered at a high yield.

9 Claims, No Drawings

METHOD FOR REMOVING VIRUSES AND LEUKOCYTES FROM BLOOD USING A SURFACE COMPRISING HYDROXYL AND POLYETHYLENE GLYCOL GROUPS

TECHNICAL FIELD

The present invention relates to a method for selectively and simultaneously removing viruses and leukocytes in blood and to a material and an apparatus for the selective removal method.

BACKGROUND ART

In conventional blood processing systems (e.g. Patent Documents 1-3), plasma component and blood cell component are separated using a plasma separation membrane or a centrifugal separator and then unnecessary substances are adsorbed and removed by directly bringing the plasma component into contact with an immunoadsorbent, a low-density lipoprotein adsorbent, or the like. In these systems, it is difficult to remove unnecessary substances, such as viruses, and leukocytes simultaneously since the blood cell components such as erythrocytes, Leukocytes, and platelets are collectively separated from the plasma component. Further, in these systems, platelets are activated because these systems use a material having charges. Therefore, it is impossible to recover platelets at a high recovery rate at the same time while removing unnecessary substances and leukocyte.

Patent Document 4 describes a method for purifying blood of a patient with an immunologic disease by simultaneously removing leukocytes and malignant substances such as immunoglobulin from the blood using a material for removing leukocyte. However, the specification describes neither simultaneous removal of leukocytes and viruses nor recovery of platelets to be performed simultaneously with the removal of leukocytes and viruses.

Patent Document 5 describes an apparatus and a method for processing blood, comprising removing a target substance such as a virus from the blood without using an anticoagulant by treating blood with a carrier having a polyamine and an anticoagulant on the surface. However, it is difficult to recover a sufficient amount of platelets, since the surface of the carrier has a large amount of the amine. Also, the degree of removing leukocytes is not sufficient.

As a material for removing a virus, Patent Document 6 describes a material having a cationic compound on the surface. However, the specification does not describe removal of a virus from blood at all. Patent Document 7 describes a material for removing HIV and its related substances, the material having the surface of a weak acidic or weak basic solid substance. This removing material is characterized by having —COOH, —SO$_3$H, or the like on the surface and a surface pH of 2.5-6.9 or 7.4-10.5. The specification describes that a virus cannot be removed when —COOH, —SO$_3$H, or the like on the surface forms a salt. Furthermore, in the method described in Patent Document 7, denaturation or the like of the component protein occurs, which is not favorable for blood, since the pH of blood changes when the blood comes in contact with the removing material. As a problem common to these techniques, there is a risk of blood coagulation due to denaturation of a blood protein when blood comes in contact with a removing material.

(Patent Document 1) Japanese Patent Application Laid-open No. 61-113463

(Patent Document 2) Japanese Patent Publication No. 05-50302

(Patent Document 3) Japanese Patent Publication No. 05-50303

(Patent Document 4) Japanese Patent Publication No. 05-50301

(Patent Document 5) Japanese Patent Application Laid-open No. 11-267199

(Patent Document 6) Japanese Patent Application Laid-open No. 03-123630

(Patent Document 7) Japanese Patent Application Laid-open No. 02-36878

DISCLOSURE OF THE INVENTION

An object of the present invention is to solve the above problems in the prior arts. In particular, an object of the present invention is to provide a method that can simultaneously remove viruses and leukocytes from virus-containing blood and can achieve a high platelet recovery rate, and to provide a material and an apparatus for the method.

As a result of extensive studies to achieve the above object, the present inventors have found that viruses and leukocytes can be simultaneously removed from blood and platelets can be recovered at a high recovery rate by bringing virus-containing blood into contact with a water-insoluble carrier of which the surface can remove viruses and leukocytes in blood. This finding has led to the present invention. Further, the present inventors have found that leukocytes and viruses can be simultaneously removed effectively by using a material that can increase the concentration of an activated complement C3a by five times or more when blood is brought into contact with the material. This has led to the completion of the present invention.

Specifically, the present invention relates to a method for selectively removing viruses and leukocytes simultaneously from blood, comprising a step of bringing virus-containing blood into) contact with a material for selectively removing viruses and leukocytes which comprises a water-insoluble carrier having a surface for adsorbing or removing viruses and leukocytes in blood.

The present invention also relates to a platelet-permeable material for selectively and simultaneously removing viruses and leukocytes from blood, comprising a water-insoluble carrier having a surface for adsorbing or removing viruses and leukocytes in blood.

The present invention further provides an apparatus for selectively removing viruses and leukocytes, comprising a container having a blood inlet section and a blood outlet section in which the material for selectively removing viruses and leukocytes is placed, and means for preventing the material from escaping from the container.

The method, the removing material, and the apparatus are particularly useful when the blood contains hepatitis C virus.

It is most preferable that the platelet-permeable material for selectively removing viruses and leukocytes has a terminal hydrophilic group or a combination of a terminal hydrophilic group and a polyethylene glycol group and, in addition, a further terminal hydrophobic group on the surface of the carrier.

BEST MODE FOR CARRYING OUT THE INVENTION

The present invention will be described in detail below.

In the present invention, a virus includes a free virus in blood, a protein-bound virus, a virus in infected leukocytes, and, the like.

Specifically, substances to be removed in the present invention include viruses, protein-bound viruses, and the like in blood. Any viruses such as hepatitis A virus, hepatitis B virus, hepatitis C virus, and HIV can be removed. Of these, the hepatitis C virus can be removed at a particularly high efficiency. It may be assumed, although not definitively proven, that the hepatitis C virus can be removed at the same high efficiency as leukocytes, due to surface properties and the size of the virus. Examples of the hepatitis C virus include hepatitis C virus in blood, hepatitis C virus adsorbed in immunoglobulin or the like, hepatitis C virus adsorbed in plasma protein, and leukocytes such as lymphocytes activated by hepatitis C virus, macrophage in an inflamed part, and granulocytes. Especially when the viruses and pharmaceutical such as interferon are removed simultaneously, the viruses that can be previously removed using the method of the present invention are hepatitis C virus, hepatitis C virus adsorbed on a plasma protein, leukocytes infected by hepatitis C virus, and autoreactive T cells activated by hepatitis C virus. In particular, with regard to leukocytes, it is more advantageous to remove lymphocytes, since the lymphocyte is infected with the hepatitis C virus.

In the present invention, blood includes blood components such as plasma and serum.

When blood is treated, it is possible to add an anticoagulant to the blood for the purpose of preventing coagulation. The anticoagulant is not specifically limited in as much as the anticoagulant is a compound having anticoagulant activity. As a preferable example of the anticoagulant, heparin, Futhan, FOY, Argatroban, citric acid and the like can be given. Of these, heparin and Futhan are particularly preferably used.

In the present invention, removal of viruses or leukocytes means to be removed from blood by adsorbing and/or filtering the viruses or leukocytes. Any methods such as a standing method, shaking method, adsorption method using diffusion, and filtration method may be employed for bringing blood into contact with a material for removing viruses and leukocytes. For adsorption and filtration, a method of causing blood to flow by a head drop, using a pump, or the like is advantageously used.

It has been found unexpectedly that the material for removing viruses and leukocytes of the present invention preferably has at least a terminal hydrophilic group on the surface. As the terminal hydrophilic group on the surface of the carrier of the material for removing viruses and leukocytes, a uncharged neutral functional group is preferably used. Examples of such a preferable functional group include a hydroxyl group, hydroxyl group-containing alkyl groups such as a hydroxymethyl group, hydroxyethyl group, hydroxypropyl group, hydroxyisopropyl group, hydroxybutyl group, and hydroxyisobutyl group, and methoxypolyethylene glycol groups such as a methoxydiethylene glycol group and methoxytriethylene glycol group. Of these, a hydroxyl group, hydroxypropyl group, hydroxyisopropyl group, and hydroxyisobutyl group are particularly preferably used.

To improve permeability of platelets, a methoxydiethylene glycol group or methoxytriethylene glycol group is preferably used.

To improve both the removal rate of viruses and leukocytes and the platelet recovery rate, it is most preferable to use a hydroxyl group, hydroxypropyl group, hydroxyisopropyl group, or hydroxyisobutyl group in combination with a methoxydiethylene glycol group or methoxytriethylene glycol group.

In the present invention, a terminal means a terminal of a main chain or a terminal of a side chain. The terminal group may be bonded directly to the main chain or via an ester bond, amide bond, urethane bond, or the like. In the latter case, the terminal refers to a terminal part which does not include the bond.

As a preferable terminal hydrophobic group on the surface of the carrier of the material for removing viruses and leukocytes of the present invention, alkyl groups having 1 to less than 30 carbon atoms such as a methyl group, ethyl group, propyl group, isopropyl group, butyl group, isobutyl group, t-butyl group, pentyl group, hexyl group, heptyl group, and octynyl group, aromatic groups such as a phenyl group, aliphatic groups such as a cyclopentyl group and cyclohexyl group, and the like can be given. In view of permeability of platelets, alkyl groups having 10 to less than 30 carbon atoms, i.e. alkyl group such as a methyl group, and an ethyl group are more preferable. Alkyl groups having 10 to less than 20 carbon atoms, a methyl group, and an ethyl group are most preferable.

In the material for selectively removing viruses and leukocytes of the present invention, the hydrophilic group is effectively used for adsorbing/removing hydrophilic protein-adsorbed viruses and leukocytes and for improving recovery capability for platelets.

The hydrophobic group is effectively used for improving adsorption of viruses or hydrophobic protein-adsorbed viruses. In the material for removing viruses and leukocytes of the present invention, to remove viruses and leukocytes and maintain permeability of platelets, it is important to ensure a well balanced proportion of the terminal hydrophilic groups and the terminal hydrophobic groups. Excessive hydrophobicity is disadvantageous for recovery of platelets.

The percentage of the terminal hydrophilic groups is preferably 2% or more, and less than 100%. When the percentage of the terminal hydrophilic groups is less than 2%, hydrophobicity is high. In this case, leukocytes and viruses can be adsorbed, whereas permeability of platelets unpreferably decreases extremely. If the percentage of the hydrophilic groups is 100%, adsorption of viruses unpreferably decreases. From the above standpoint, the percentage is more preferably 3% or more, and less than 90%, and most preferably 5% or more, and less than 80%.

The percentage of the terminal hydrophobic groups is also important When the percentage is 0.19 or more, and less than 70%, the material is advantageously used. When the percentage of the terminal hydrophobic groups is 70% or more, the platelet recovery rate is unpreferably reduced. If the percentage is less than 0.1%, adsorption of a virus-adsorbing protein unpreferably decreases due to the low hydrophobicity. For these reasons, the percentage is more preferably 1% or more, and less than 60%, and most preferably 1% or more, and less than 55%.

In the present invention, the percentages of the terminal hydrophilic groups and the terminal hydrophobic groups refer to the percentages of the hydrophilic groups and the hydrophobic groups on the surface of the material for removing viruses and leukocytes, specifically, the molar ratios of the functional groups of the carrier coming in contact with blood. The percentages of these terminal groups can be determined by solid state nuclear magnetic resonance spectroscopy, infrared absorption spectroscopy, XPMS, ESCA, or the like known in the art. When the surface of the carrier is modified by coating or the like, the percentages of the terminal groups in the coating polymer can be indicated in molar ratios.

In the present invention, the surface refers to the surface of the material with which viruses or the like can come in contact and excludes the inside of the material with which viruses cannot come in contact. In the present invention, the surface of the carrier can have a function of capturing viruses and leukocytes in blood and allowing platelets to permeate therethrough insofar as the surface of the carrier is provided with the terminal hydrophilic groups. The terminal hydrophilic groups may be provided by coating the surface with a material containing the terminal hydrophilic groups, or by introducing the functional groups into the surface of the carrier by radiation graft polymerization, covalent bonding, or the like. It is also possible to use a material having the functional groups on the surface as a carrier.

The material for removing viruses and leukocytes having the terminal hydrophilic groups can have terminal cationic groups on the surface of the carrier. The terminal cationic group is particularly advantageously used for improving adsorption of a virus having negative charges on the surface.

Examples of the terminal cationic group include tertiary amino groups formed by bonding of a dimethylamino group, diethylamino group, dipropylamino group, or the like to the terminal, of the main chain or side chain of a polymer, and aromatic groups such as heterocyclic groups. Of these, a dimethylamino group, diethylamino group, and the like are advantageously used. If the terminal cationic group is a primary or secondary amino group, ionicity is strong, unpreferably resulting in a reduction in the platelet recovery rate.

The percentage of the terminal cationic groups is preferably less than 15%. If the percentage exceeds 15%, the platelet recovery rate is reduced due to the excessive amount of the cationic groups. The percentage is more preferably less than 13%, and most preferably less than 11%.

It has been found that leukocytes and viruses can be simultaneously removed most effectively when the material for removing viruses and leukocytes of the present invention is a material that can increase the concentration of an activated complement C3a by five times or more after bringing blood into contact with the material. It has also been found that viruses can be easily adsorbed under the influence of forming a complex with the activated complement C3a, whereas an excessive increase in the concentration of the activated complement C3a relatively reduces the concentration of the viruses, resulting in a decrease in adsorption of the viruses. When the increase in the concentration of the activated complement C3a is less than five times after blood has been brought into contact with the material, removing capability of viruses and leukocytes unpreferably decreases extremely. When the concentration of the activated complement C3a increases by five times or more after bringing blood into contact with the material, effectiveness of the material is ensured. However, when the concentration of the activated complement C3a increases by 1,000 times or more after bringing blood into contact with the material, the material cannot be used in practice due to anaphylaxis or the like caused by the complement. When the concentration of the activated complement C3a increases by 500 times or more, the component composition of blood significantly unpreferably changes. The concentration of the activated complement C3a increases by more preferably seven times or more, and most preferably by ten times or more, after bringing blood into contact with the material.

As the material for increasing the concentration of the activated complement C3a by five times or more after bringing blood into contact with the material, a material having 5 mol % or more of the above-described terminal hydrophilic groups on the surface is used. Examples of the terminal hydrophilic group-containing monomer include, as terminal hydrophilic group monomers, hydroxyalkyl methacrylates such as 2-hydroxyethyl methacrylate, 2-hydroxypropyl methacrylate, 2-hydroxyisopropyl methacrylate, 2-hydroxybutyl methacrylate, and 2-hydroxyisobutyl methacrylate, and methoxypolyethylene glycol methacrylates such as methoxydiethylene glycol methacrylate, methoxytriethylene glycol methacrylate, and methoxytetraethylene glycol methacrylate.

A polymer obtained by copolymerizing or terpolymerizing these monomers is effectively used for activation. Examples of the polymer include a random copolymer of 2-hydroxyisobutyl methacrylate (HBMA), methoxydiethylene glycol methacrylate (MDG), and methyl methacrylate (MMA) (copolymerization molar ratio, HBMA:MDG:MMA=5-40:5-30:40-60), a random copolymer of 2-hydroxyisopropyl methacrylate (HPMA), methoxydiethylene glycol methacrylate, and methyl methacrylate (copolymerization molar ratio, HPMA:MDG:MMA=5-40:5-30:40-70), and a random copolymer of HPMA and dimethylaminoethyl methacrylate (DM) (copolymerization molar ratio, HPMA:DM=80-93:3-20).

In particular, a random copolymer of 2-hydroxyisobutyl methacrylate (HBMA), methoxydiethylene glycol methacrylate (MDG), and methyl methacrylate (MMA) (copolymerization molar ratio, HBMA:MDG:MMA=5-40:5-30:40-60) is most advantageously used.

A material with inherent characteristics that can increase the concentration of the activated complement C3a by five times or more after bringing blood into contact with the material is also effectively used. Such a material has the hydrophilic groups on the surface. Examples of the material advantageously used include natural polymers such as cellulose and/or its derivatives, and polymeric materials such as polyesters including polyethylene terephthalate and polybutylene terephthalate, an ethylene-vinyl alcohol copolymer and polyurethane. In view of activation, particularly preferably, polyesters such as polyethylene terephthalate and polybutylene terephthalate, an ethylene-vinyl alcohol copolymer, cellulose, and the like can be given, most preferably, polyesters such as polyethylene terephthalate and polybuthylene terephthalate are advantageously used.

As the carrier of the material for selectively removing viruses and leukocytes used in the present invention, particles, beads, a porous material, a flat membrane, a nonwoven fabric, a woven fabric, or the like can be given, for example. Of these, a porous material and a nonwoven fabric are preferably used, since these carriers can remove viruses and leukocytes simultaneously and have a large surface area. A nonwoven fabric is most preferable.

The constituent of the carrier is not specifically limited insofar as the carrier can be subjected to surface treatment. Examples of the constituent include natural polymers such as cellulose and/or its derivatives, and polymeric materials such as polyesters including polyethylene terephthalate and polybutylene terephthalate, polyolefins including polyethylene and polypropylene, polyvinylidene fluoride, polyamide polyimide, polyurethane, polysulfone, and polyacrylonitrile.

The nonwoven fabric can be employed as is, when the nonwoven fabric has affinity with viruses and leukocytes without surface modification. When the nonwoven fabric does not have such affinity without surface modification, the nonwoven fabric is preferably subjected to surface modification such as coating to provide affinity.

In particular, to improve adsorption and/or removal of target substances and leukocytes and recovery of platelets, a nonwoven fabric of which the surface is modified by a treatment such as coating is preferably used.

When the carrier is a nonwoven fabric, the filament may be either a monofilament or a multifilament, or either a porous filament or an irregular filament.

The average fiber diameter of the nonwoven fabric is preferably 2.0 μm or more, and less than 50 μm. If the fiber diameter is too large, it is difficult to secure the surface area of the base material. This unpreferably results in a reduction in the area for adsorbing viruses and a decrease in leukocyte removing capability.

If the fiber diameter is too small, clogging easily occurs in the removing material and platelets are recovered only with difficulty. For these reasons, the average fiber diameter is more preferably 2.0 μm or more, and less than 30 μm, and most preferably 2.3 μm or more, and less than 20 μm.

To improve removal of leukocytes and permeability of platelets, it is also important that the bulk density of the nonwoven fabric be 0.10 g/cm$^3$ or more, and less than 0.45 g/cm$^3$. If the bulk density is less than 0.10 g/cm$^3$, the removing capability of leukocytes decreases. If the bulk density is 0.45 g/cm$^3$ or more, permeability of platelets decreases extremely. For these reasons, the bulk density is preferably 0.15 g/cm$^3$ or more, and less than 0.45 g/cm$^3$, and most preferably 0.15 g/cm$^3$ or more, and less than 0.40 g/cm$^3$.

For nonwoven fabric, to improve adsorption of viruses, removal of leukocytes, and permeability of platelets, it is also important that the specific surface area of the nonwoven fabric be 0.010 m$^2$/g or more, and less than 4.0 m$^2$/g. If the specific surface area is less than 0.01 m$^2$/g, the removal capability of viruses and leukocytes decreases. If the specific surface area is 4.0 m$^2$/g or more, permeability of platelets decreases extremely. For these reasons, the specific surface area is preferably 0.02 m$^2$/g or more, and less than 3.0 m$^2$/g, and most preferably 0.04 m$^2$/g or more, and less than 2.5 m$^2$/g.

As the surface-modified compound that can remove viruses and leukocytes and recover platelets at a high recovery rate, a polymer compound having a terminal hydrophilic group on the side chain and a polymer compound having a terminal hydrophilic group and a terminal hydrophobic group on the side chain at the same time can be given.

Examples of the monomer forming those polymer compounds include, as terminal hydrophilic group monomers, hydroxyalkyl methacrylates such as 2-hydroxyethyl methacrylate, 2-hydroxypropyl methacrylate, 2-hydroxyisopropyl methacrylate, 2-hydroxybutyl methacrylate, and 2-hydroxyisobutyl methacrylate, and methoxypolyethylene glycol methacrylates such as methoxydiethylene glycol methacrylate, methoxytriethylene glycol methacrylate, and methoxytetraethylene glycol methacrylate.

As examples of terminal hydrophobic group monomers, alkyl methacrylates such as methyl methacrylate, ethyl methacrylate, propyl methacrylate, butyl methacrylate, and octadecyl methacrylate, and aromatic methacrylates such as benzyl methacrylate and phenyl methacrylate can also be given.

Even if the above polymerizable functional groups are vinyls, acrylates, or the like, they can be effectively used.

The surface coating material used in the present invention can be effectively obtained by copolymerizing two kinds of monomers or terpolymerizing three kinds of monomers according to the percentages of the hydrophilic groups and the hydrophobic groups.

Particularly preferable examples of the copolymer using the monomers include a copolymer of methoxydiethylene glycol methacrylate, 2-hydroxyisobutyl methacrylate, and methyl methacrylate.

Examples of the terminal cationic group monomer when the terminal cationic group is introduced include dialkylaminoalkyl methacrylates such as dimethylaminoethyl methacrylate and diethylaminoethyl methacrylate.

These exemplified polymer compounds can be effectively used directly as a base material or used by coating on the surface of a base material.

In addition, these monomers may be effectively used as is or may be effectively used after polymerizing or copolymerizing monomers such as glycidyl methacrylate and then appropriately introducing a necessary terminal group into the polymer.

Various conventional methods can be used as the method for providing the surface of the carrier with a hydroxyl group, a polyethylene glycol group, a hydrophobic group, and a neutral group. To provide the surface of the carrier with such groups means that the groups must be caused to be present on the surface so as not to be eluted into water or blood. Examples of the method include graft polymerization, coating, and a method comprising introducing a functional group such as an epoxy group, amino pinup, formyl group, carboxyl group, hydroxyl group, acid halide group, or cyanogen halide group into the surface of the carrier and bonding the functional group to the compound which should possess the target functional group directly or via a coupling agent or a spacer.

The material for removing viruses and leukocytes of the present invention can be more suitably used in the blood processing apparatus of the present invention. The apparatus for removing viruses and leukocytes of the present invention is an apparatus for adsorbing and/or removing a virus, a protein bound virus, and leukocytes from blood, comprising a container having a blood inlet section and a blood outlet section in which the material for selectively removing viruses and leukocytes is included, and a means for preventing the material for removing viruses and leukocytes from escaping from the container.

As the means for preventing the removing material from escaping from the container, any means through which all blood components can pass but through which the removing material cannot pass can be used. The means can be a mesh, filter, or the like, having a mesh size smaller than the diameter of the removing material, installed in at least the outlet port of the container. When a fiber such as a nonwoven fabric is used as the carrier, the means which the nonwoven fabric may be bonded to the upper end or lower end of the container using an adhesive, or inserted in a clearance between the containers can be adopted, in addition to providing the above-described mesh. In particular, when a cylindrical depth filter is used, one end of the cylinder is blocked and the other end on the outlet port side is connected to a nozzle or the like. As the adhesive used, an adhesive of which bonding strength is not weakened by swelling or the like when the adhesive comes in contact with a liquid such as blood is preferable. For example, a urethane-based adhesive and an epoxy-based adhesive are advantageously used. However, the adhesive used is not limited to these.

The apparatus of the present invention can be particularly advantageously used if connected with a blood collection means, an anticoagulant mixing means, a retransfusion means, and the like via a tube.

The housing of the apparatus of the present invention is preferably formed from a synthetic resin such as polypropylene, polycarbonate, polyethylene, polystyrene, or polymethacrylic acid, glass, or a metal such as stainless steel.

EXAMPLES

The present invention is described below with reference to experimental examples and examples. However, the present invention is not limited to these examples.

Experimental examples for producing a polymer used for modifying the surface of the carrier in the present invention will be described.

Experimental Example 1

A random copolymer of 2-hydroxyisobutyl methacrylate (HBMA), methoxydiethylene glycol methacrylate (MDG), and methyl methacrylate (MMA) was synthesized using a conventional radical polymerization initiator. The polymerization was carried out at 70° C. for six hours using MDG monomer, HBMA monomer, and MMA monomer (MDG:HBMA:MMA=30:20:50, in molar ratio), 300 ml of ethanol, and 0.1 g of azobisvaleronitrile (V-65) as an initiator. The obtained polymer solution was added dropwise to 10 l of water while stirring. The copolymer was precipitated and the water-insoluble components were collected. The composition ratio of the obtained copolymer was the same as the mixing ratio of the monomers. Accordingly, the percentages of the terminal hydrophilic groups and the terminal hydrophobic groups in the copolymer were respectively 50% and 50%.

Experimental Example 2

A copolymer of 2-hydroxyisopropyl methacrylate (HPMA) and dimethylaminoethyl methacrylate (DM) was produced in the same manner as in Experimental Example 1. The molar ratio HPMA:DM of the copolymer was of 97:3. The percentages of the terminal hydrophilic groups and the terminal cationic groups in the copolymer were respectively 97% and 3%.

Experimental Example 3

A copolymer of 2-hydroxyethyl methacrylate (HPMA), dimethylaminoethyl methacrylate (DM), and methyl methacrylate (MMA) was produced in the same manner as in Experimental Example 1. The molar ratio HEMA:MMA:DM of the copolymer was 62:30:8. The percentages of the terminal hydrophilic groups, the terminal hydrophobic groups, and the terminal cationic group in the copolymer were respectively 62%, 30%, and 8%.

Examples of the blood processing system for hepatitis C will be described below. However, the present invention is not limited to these examples.

Example 1

1 g of the copolymer obtained in Example 1 was dissolved in 99 g of 70% aqueous solution of ethanol to obtain a 1% coating solution. 1 g of a nonwoven fabric (the weight of the substrate per unit area (Metsuke): 90 g/m$^2$, thickness: 0.40 mm, bulk density: 0.24 g/cm$^3$, specific surface area: 0.966 m$^2$/g) comprising a polyethylene terephthalate fiber with an average fiber diameter of 2.9 μm was immersed in 10 ml of the 1% coating solution, followed by drying the mixture at 25° C. for 12 hours.

0.01 g of the obtained nonwoven fabric was cut into strips and collected in a vial. 1 ml of blood of a patient containing hepatitis C virus was added to the vial. The vial was shaken at 37° C. for two hours.

Next, 100 μl of the blood after the above treatment was sampled in a vial and centrifuged at 5,000 rpm for one minute. The amount of hepatitis C virus in the supernatant liquid was determined as HCVRNA. The amount of hepatitis C virus was determined using Amplicor HCV Monitor manufactured by Nippon Roche K. K.

The number of leukocytes and the number of platelets in the treated blood were determined using an automatic blood cell counter (SF-3000, manufactured by Sysmex Corporation).

The concentrations of the activated complement C3a before and after treatment were measured by nephelometric analysis to determine the rate of increase in the concentration for the value after treatment as compared with the value before treatment.

As a control experiment, the same operation as in Example 1 was carried out without using the removing material of the present invention.

The hepatitis C virus adsorption rate (%), the leukocyte removal rate (%), and the platelet recovery rate (%) were calculated using the following equations.

Virus adsorption rate (%)=[(Vd−Vc)/Vd]×100

Vc: Virus concentration in blood of control experiment
Vd: Virus concentration in blood of adsorption experiment Leukocyte removal rate (%)=[(Wd−Wc)/Wd]×100

Wc: Leukocyte concentration in blood of control experiment
Wd: Leukocyte concentration in blood of adsorption experiment Platelet recovery rate (%)=Pd/Pc×100

Pc: Platelet concentration in blood of control experiment
Pd: Platelet concentration in blood of adsorption experiment The results are shown in Table 1. The results of the control experimental example not using the removing material are also shown in Table 1. It can be seen that the number of leukocytes and the number of platelets in the control experimental example were reduced to some extent due to attachment of leukocytes and platelets to the container or the like.

Example 2

The same operation as in Example 1 was carried out except for using a nonwoven fabric (the weight per unit area (Metsuke): 60 g/m$^2$, thickness: 0.35 mm, bulk density: 0.12 g/cm$^3$, specific surface area: 1.768 m$^2$/g) comprising a polypropylene fiber with an average fiber diameter of 2.5 μm. The results are shown in Table 1.

TABLE 1

| | Virus adsorption rate | Leukocyte removal rate | Platelet recovery rate | C3a concentration |
|---|---|---|---|---|
| Example 1 | 85% | 80% | 90% | 11.6 times |
| Example 2 | 89% | 82% | 94% | 18.5 times |
| Control Experimental Example | 0% | 1% | 98% | 2.3 times |

Comparative Example 1

The same operation as in Example 1 was carried out except for using a nonwoven fabric (the weight per unit area: 90 g/m$^2$, thickness 0.40 mm) comprising a polyethylene terephthalate fiber with an average fiber diameter of 2.9 μm as is. The result are shown in Table 2.

Comparative Example 2

The same operation as in Example 1 was carried out except for using a nonwoven fabric (the weight per unit area: 60 g/m$^2$, thickness: 0.35 mm) comprising a polypropylene fiber with an average fiber diameter of 2.5 μm as is. The results are shown in Table 2.

TABLE 2

|  | Virus adsorption rate | Leukocyte removal rate | Platelet recovery rate | C3a concentration |
| --- | --- | --- | --- | --- |
| Comparative Example 1 | 58% | 84% | 21% | 3.5 times |
| Comparative Example 2 | 63% | 80% | 18% | 1.8 times |

Example 3

The removing material of Example 1 was cut into disks, each with a diameter of 6.8 mm. Five sheets of the disks were respectively placed in a column. The hepatitis C virus adsorption rate, the leukocyte removal rate, and the platelet recovery rate were evaluated.

1.5 ml of fresh human blood (amount of virus: 100,000 copies/ml, number of leukocytes: 4,500-8,400/μl, number of platelets: 150,000-440,000/μl) to which ACD-A was added as a anticoagulant (blood:ACD-A=8:1) was flowed into each column using a syringe pump at a constant flow rate of 0.5 ml/min at room temperature. The concentrations of viruses, leukocytes, and platelets in blood before and after the blood permeation through the nonwoven fabric were respectively measured to determine the virus adsorption rate, the leukocyte removal rate, and the platelet recovery rate in the same manner as in Example 1. The results are shown in Table 3.

Example 4

The same operation as in Example 3 was carried out, except for using, the removing material of Example 2. The results are shown in Table 3.

TABLE 3

|  | Virus adsorption rate | Leukocyte removal rate | Platelet recovery rate | C3a concentration |
| --- | --- | --- | --- | --- |
| Example 3 | 91% | 95% | 70% | 12.5 times |
| Example 4 | 94% | 97% | 75% | 23.5 times |

Comparative Example 3

The same operation as in Example 3 was carried out, except for using the material of Comparative Example 1. The results are shown in Table 4.

Comparative Example 4

The same operation as in Example 3 was carried out, except for using the material of Comparative Example 2. The results are shown in Table 4.

TABLE 4

|  | Virus adsorption rate | Leukocyte removal rate | Platelet recovery rate | C3a concentration |
| --- | --- | --- | --- | --- |
| Comparative Example 3 | 60% | 98% | 8% | 4.8 times |
| Comparative Example 4 | 75% | 97% | 6% | 2.3 times |

Example 5

The same operation as in Example 1 was carried out using the same nonwoven fabric as in Example 1 to obtain a removing material, except for using the polymer produced in Experimental Example 2 for coating. Blood was treated in the same manner as in Example 1 and the hepatitis C virus adsorption rate, the leukocyte removal rate, and the platelet recovery rate were evaluated.

The results are shown in Table 5.

Example 6

The same operation as in Example 1 was carried out using the same nonwoven fabric as in Example 1 to obtain a removing material, except for using the polymer produced in Experimental Example 3 for coating. Blood was treated in the same operation as in Example 1 and the hepatitis C virus adsorption rate, the leukocyte removal rate, and the platelet recovery rate were evaluated.

The results are shown in Table 5.

TABLE 5

|  | Virus adsorption rate | Leukocyte removal rate | Platelet recovery rate | C3a concentration |
| --- | --- | --- | --- | --- |
| Example 5 | 79% | 89% | 87% | 19.5 times |
| Example 6 | 91% | 95% | 86% | 22.5 times |

Example 7

The same nonwoven fabric as in Example 1 was cut into a sheet (width: 150 mm, length: 300 mm) and the sheet was wound around a cylindrical mesh with a diameter of 3.4 mm made from polyethylene. Next, a nonwoven fabric (the weight per unit area: 30 g/m$^2$) comprising a polyester fiber with an average fiber diameter of 12 μm was provided as the first prefilter. The first prefilter with a width of 150 mm was wound around the above nonwoven fabric. Further, a nonwoven fabric (the weight per unit area: 50 g/m$^2$) comprising a polyester fiber with an average fiber diameter of 33 μm was provided as the second prefilter. The second prefilter with a width of 150 mm was wound around the first prefilter. A mesh with a width of 150 mm made from polyethylene was wound around the second prefilter. The cylinder thus formed had a diameter of 39 mm. Both ends of the cylinder were blocked by urethane. The cylinder was placed in a cylindrical polycarbonate container with an internal diameter of 41 mm of which the top and the bottom were respectively provided with a blood inlet port and a blood outlet port, so that the outer circumference of the cylinder was connected to the blood inlet port of the container and the inner circumference of the cylinder was connected to the blood outlet port of the container. An apparatus for removing leukocytes was thus produced.

50 ml of plasma containing hepatitis C virus was added to 2,000 ml of fresh bovine blood (number of leukocytes: 4,500-6,400/µL, number of platelets: 150,000-320,000/µL) to which heparin was added as a anticoagulant (heparin concentration: 1,000 IU/L) (amount of virus: 2,500,000/l). The mixture was fed into the apparatus using a blood pump at a constant flow rate of 50 ml/min at room temperature to remove leukocytes. The concentrations of viruses, leukocytes, and platelets in blood before and after 2,000 ml of the blood permeation through the apparatus for removing leukocytes were respectively measured to determine the virus adsorption rate, the leukocyte removal rate, and the platelet recovery rate in the same manner as in Example 1. The results are shown in Table 6.

TABLE 6

|  | Virus adsorption rate | Leukocyte removal rate | Platelet recovery rate |
| --- | --- | --- | --- |
| Example 7 | 69% | 93% | 62% |

INDUSTRIAL APPLICABILITY

As is clear from Examples above, the present invention can provide a material for removing viruses and leukocytes that can selectively adsorb and/or remove viruses and leukocytes in blood. When a blood processing apparatus comprising the removing material is used, hepatitis C viruses and leukocytes in a liquid to be processed such as blood, plasma, or serum can be selectively removed and platelets can be recovered at a high recovery rate.

The invention claimed is:

1. A method for selectively and simultaneously removing free and/or protein-bound viruses and leukocytes from blood, comprising:

bringing virus-containing blood into contact with a material for selectively removing viruses and leukocytes, said material for selectively removing viruses and leukocytes comprising a water-insoluble carrier having a surface which captures viruses and leukocytes in blood and allows platelets in blood to permeate therethrough, said surface comprising at least a hydroxyl group and a polyethylene glycol group.

2. The method according to claim 1, wherein the virus-containing blood is brought into contact with the material for selectively removing viruses and leukocytes by using an adsorption method and/or a filtration method.

3. The method according to claim 1, further comprising:

mixing the virus-containing blood with an anticoagulant, and bringing the virus-containing blood mixed with the anticoagulant into contact with the material for selectively removing viruses and leukocytes at a flow rate of 10 ml/min to 100 ml/min.

4. The method according to claim 1, wherein the leukocytes to be removed include at least lymphocytes.

5. The method according to claim 1, wherein the leukocytes to be removed include at least autoreactive T cells.

6. The method according to claim 1, wherein the material for selectively removing viruses and leukocytes has a capability of increasing the concentration of an activated complement C3a in blood by five times or more after being brought into contact with the blood.

7. The method according to claim 1, wherein the water-insoluble carrier is fibrous.

8. The method according to claim 7, wherein the carrier for removing leukocytes is a nonwoven fabric.

9. The method according to claim 1, wherein the viruses are hepatitis C viruses.

* * * * *